US009688649B2

(12) United States Patent
Iyer et al.

(10) Patent No.: US 9,688,649 B2
(45) Date of Patent: Jun. 27, 2017

(54) AMIDE-LINKED PERFLUOROPOLYETHER THIOL COMPOUNDS AND PROCESSES FOR THEIR PREPARATION AND USE

(71) Applicant: 3M INNOVATIVE PROPERTIES COMPANY, St. Paul, MN (US)

(72) Inventors: Suresh S. Iyer, Woodbury, MN (US); Mark J. Pellerite, Woodbury, MN (US); Chetan P. Jariwala, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 140 days.

(21) Appl. No.: 14/527,877

(22) Filed: Oct. 30, 2014

(65) Prior Publication Data

US 2015/0051362 A1 Feb. 19, 2015

Related U.S. Application Data

(62) Division of application No. 13/132,673, filed as application No. PCT/US2009/066337 on Dec. 2, 2009, now Pat. No. 8,901,263.

(60) Provisional application No. 61/121,598, filed on Dec. 11, 2008, provisional application No. 61/121,605, filed on Dec. 11, 2008.

(51) Int. Cl.
*C07C 323/41* (2006.01)
*C07C 323/60* (2006.01)
*C07D 303/48* (2006.01)
*B05D 1/18* (2006.01)
*B82Y 30/00* (2011.01)
*B82Y 40/00* (2011.01)
*C07C 323/52* (2006.01)
*C08G 65/00* (2006.01)
*C08G 65/334* (2006.01)
*C09D 171/02* (2006.01)
*G03F 7/00* (2006.01)
*B82Y 10/00* (2011.01)
*C08F 2/38* (2006.01)

(52) U.S. Cl.
CPC .......... *C07D 303/48* (2013.01); *B05D 1/185* (2013.01); *B82Y 10/00* (2013.01); *B82Y 30/00* (2013.01); *B82Y 40/00* (2013.01); *C07C 323/41* (2013.01); *C07C 323/52* (2013.01); *C07C 323/60* (2013.01); *C08F 2/38* (2013.01); *C08G 65/007* (2013.01); *C08G 65/334* (2013.01); *C09D 171/02* (2013.01); *G03F 7/0002* (2013.01)

(58) Field of Classification Search
USPC .......................................... 526/209; 564/154
See application file for complete search history.

(56) References Cited

U.S. PATENT DOCUMENTS

| | | | |
|---|---|---|---|
| 3,250,807 A | 5/1966 | Fritz | |
| 3,250,808 A | 5/1966 | Moore | |
| 3,810,874 A | 5/1974 | Mitsch | |
| 4,022,928 A | 5/1977 | Piwcyzk | |
| 4,204,064 A | 5/1980 | Kalopissis | |
| 4,845,268 A | 7/1989 | Ohsaka | |
| 4,882,216 A | 11/1989 | Takimoto | |
| 4,904,417 A | 2/1990 | Ohsaka | |
| 5,182,342 A | 1/1993 | Feiring | |
| 5,354,922 A | 10/1994 | Marchionni | |
| 5,446,182 A | 8/1995 | Bruening | |
| 5,512,131 A | 4/1996 | Kumar | |
| 6,395,867 B1 * | 5/2002 | Maignan ................. | A61K 8/84 528/310 |
| 6,399,729 B1 | 6/2002 | Farnham | |
| 6,518,168 B1 | 2/2003 | Clem | |
| 6,923,921 B2 | 8/2005 | Flynn | |
| 6,991,826 B2 | 1/2006 | Pellerite | |
| 7,041,232 B2 | 5/2006 | Bietsch | |
| 7,148,360 B2 | 12/2006 | Flynn | |
| 7,160,583 B2 | 1/2007 | Frey | |
| 7,335,786 B1 | 2/2008 | Iyer | |

(Continued)

FOREIGN PATENT DOCUMENTS

JP           10-124844     *  5/1998
WO       WO 02/092660       11/2002

(Continued)

OTHER PUBLICATIONS

Saunders et al., Solvent Density-Dependent Steric Stabilization of Perfluoropolyether-Coated Nanocrystals in Supercritical Carbon Dioxide, J. Phys. Chem., B, 2004, 108(41), pp. 15969-15975.*
Smith et al., Phase Separation Within a Binary Self-Assembled Monolayer on Au{111} Driven by an Amide-Containing Alkanethiol, J. Phys. Chem. 105, 1119-1122 (2001).*
Yazdi et al., Design of Highly CO2-Soluble Chelating Agents for Carbon Dioxide Extraction of Heavy Metals, J. Mater. Res., 1995, 10(3), pp 530-537.*
Saunders et al., Solvent Density-Dependent Steric Stabilization of Perfluoropolyether-Coated Nanocrystals in Supercritical Carbon Dioxide, J. Phys. Chem., B 2004, 108(41), pp. 15969-15975.*

(Continued)

*Primary Examiner* — Mark Kaucher
*Assistant Examiner* — Henry Hu
(74) *Attorney, Agent, or Firm* — Julie Lapos-Kuchar; Lucy C. Weiss

(57) ABSTRACT

A perfluoropolyether thiol compound comprises a perfluoropolyether segment, at least one mercapto group (—SH), and at least one intervening divalent carbonylimino moiety (—C(=O)—NR—, wherein R is hydrogen or alkyl). The compound can be produced, for example, by a ring-opening reaction of thiolactones with perfluoropolyether-substituted, primary or secondary amines. The compound can be used, for example, as a polymerization chain transfer agent, as an intermediate for the preparation of functional group-containing fluorochemical derivatives such as disulfides, and as a fluorinated surface treatment.

2 Claims, No Drawings

(56) References Cited

U.S. PATENT DOCUMENTS

| | | | |
|---|---|---|---|
| 7,678,426 B2 | 3/2010 | Flynn | |
| 7,745,653 B2 | 6/2010 | Iyer | |
| 7,825,272 B2 * | 11/2010 | Iyer | C07F 7/1836 524/588 |
| 7,968,804 B2 | 6/2011 | Frey | |
| 8,901,263 B2 * | 12/2014 | Iyer | B05D 1/185 526/209 |
| 2003/0013923 A1 | 1/2003 | Marchionni | |
| 2003/0194873 A1 | 10/2003 | Imada | |
| 2003/0207215 A1 | 11/2003 | Xu | |
| 2004/0241396 A1 | 12/2004 | Jing | |
| 2005/0098433 A1 | 5/2005 | Gundel | |
| 2005/0194588 A1 | 9/2005 | Sasaki | |
| 2005/0221271 A1 | 10/2005 | Murphy | |
| 2005/0250921 A1 | 11/2005 | Qiu | |
| 2006/0035129 A1 | 2/2006 | Nomura | |
| 2007/0292679 A1 | 12/2007 | Pellerite | |
| 2008/0095985 A1 | 4/2008 | Frey | |
| 2008/0315459 A1 | 12/2008 | Zhang | |
| 2009/0025727 A1 | 1/2009 | Klun | |
| 2009/0028910 A1 | 1/2009 | DeSimone | |
| 2009/0061152 A1 | 3/2009 | DeSimone | |
| 2009/0069193 A1 | 3/2009 | Flemming | |
| 2009/0218310 A1 | 9/2009 | Zu | |
| 2010/0219367 A1 | 9/2010 | Dams | |
| 2010/0221967 A1 | 9/2010 | Iyer | |
| 2010/0258968 A1 | 10/2010 | Zu | |
| 2011/0226733 A1 | 9/2011 | Zu | |

FOREIGN PATENT DOCUMENTS

| | | |
|---|---|---|
| WO | WO 03/011915 | 2/2003 |
| WO | WO 2005/101466 | 10/2005 |
| WO | WO 2005/113642 | 12/2005 |
| WO | WO 2006/102383 | 9/2006 |
| WO | WO 2007/146855 | 12/2007 |
| WO | WO-2007/146855 A1 * | 12/2007 |
| WO | WO 2010/068531 | 6/2010 |
| WO | WO-2010/068531 A1 * | 6/2010 |
| WO | WO 2010/068535 | 6/2010 |

OTHER PUBLICATIONS

Alamarguy et al., Corrosion Behavior of Gold Surfaces Protected With Bonded Perfluoro Polyethers, Surf. Interface Anal. 36, 780 (2004).

Alamarguy et al., Surface Investigations of Bonded Perfluoro Polyether Monolayers on Gold Surfaces, Surf. Interface Anal. 36, 1210 (2004).

Blixt et al., Solid-Phase Enzymatic Synthesis of a Sialyl Lewis X Tetrasaccharide on a Sepharose Matrix, J. Org. Chem. 63, 2705 (1998).

Burdinski et al., Thiosulfate- and Thiosulfonate-Based Etchants for the Patterning of Gold Using Microcontact Printing, Chemistry of Materials 19, 3933 (2007).

Clegg et al., Control of Monolayer Assembly Structure by Hydrogen Bonding Rather Than by Adsorbate-Substrate Templating, Journal of the American Chemical Society 121, 5319 (1999).

Clegg et al., Self-Assembled Monolayers Stabilized by Three-Dimensional Networks of Hydrogen Bonds, J. Am. Chem. Soc. 120, 2486 (1998).

Clegg et al., The Interplay of Lateral and Tiered Interactions in Stratified Self-Organized Molecular Assemblies, Langmuir 15, 8876 (1999).

Colorado et al., Wettabilities of Self-Assembled Monolayers on Gold Generated From Progressively Fluorinated Alkanethiols, Langmuir 19, 3288 (2003).

Eidelloth et al, Wet Etching of Gold Films Compatible With High TC Superconducting Thin Films, Applied Physics Letters 59(13), 1632 (1991).

Evans et al., XPS Imaging of Patterned Self-Assembled Monolayers Containing Perfluorinated Alkyl Chains, Surf. Interface Anal. 24, 187 (1996).

Geissler et al., Fabrication of Metal Nanowires Using Microcontact Printing, Langmuir 19, p. 6301 (2003).

Graupe et al., Oriented Surface Dipoles Strongly Influence Interfacial Wettabilities, J. Am. Chem. Soc. 121, 3222 (1999).

J. P. Rolland et al., High-Resolution Soft Lithography: Enabling Materials for Nanotechnologies, Angewandte Chemie 43, 5796 (2004).

Kopf et al., Chemical Imaging of Microstructured Self-Assembled Monolayers With Nanometer Resolution, J. Phys. Chem. C 111, p. 8166 (2007).

Kumar et al., Features of Gold Having Micrometer to Centimeter Dimensions Can Be Formed Through a Combination of Stamping With an Elastomeric Stamp and an Alkanethiol "Ink" Followed by Chemical Etching, Appl. Phys. Lett. 63(14), p. 2002 (1993).

Laibinis et al., Comparison of the Structures and Wetting Properties of Self-Assembled Monolayers on N-Alkanethiols on the Coinage Metal Surfaces, Cu, Ag, Au, J. Am. Chem. Soc. 113(19), p. 7152 (1991).

Latham et al., Versatile Routes Toward Functional, Water-Soluble Nanoparticles Via Trifluoroethylester-Peg-Thiol Ligands, Langmuir 22, 4319 (2006).

Lee et al., Solvent Compatibility of Poly(Dimethylsiloxane)-Based Microfluidic Devices, Analytical Chemistry vol. 75, pp. 6544-6554 (2003).

Lenk et al., Structural Investigation of Molecular Organization in Self-Assembled Monolayers of a Semifluorinated Amidethiol, Langmuir 10, 4610 (1994).

Libioulle et al., Contact-Inking Stamps for Microcontact Printing of Alkanethiols on Gold, Langmuir vol. 15, pp. 300-304 (1999).

Love et al., Self-Assembled Monolayers of Thiolates on Metals As a Form of Nanotechnology, Chemical Reviews vol. 105, pp. 1103-1169 (2005).

Luscombe et al., Synthesis of Supercritical Carbon Dioxide Soluble Perfluorinated Dendrons for Surface Modification, J. Org. Chem. (2007).

Masuda et al., Visualization of DNA Hybridization on Gold Thin Film by Utilizing the Resistance Effect of DNA Monolayer, Sensors and Actuators B 105, 556 (2005).

Michel et al., Printing Meets Lithography: Soft Approaches to High-Resolution Patterning, IBM J. Res. & Dev. 45(5), p. 697 (2001).

Michel, Printing Meets Lithography, *American Institute of Physics*, Aug./Sep. 2002, pp. 16-19.

Naud et al., Critical Influence of the Fluorinated Chain Length in the Self-Assembly of Terminally Perfluorinated Alkanethiol Monolayers on Gold Surfaces. An Electrochemical Study, Langmuir 17, 4851 (2001).

Paulini et al., Effects of Branched Ligands on the Structure and Stability of Monolayers on Gold Nanoparticles, Langmuir 18, 2368 (2002).

Ramette et al., Thermodynamics of Iodine Solubility and Triiodide Ion Formation in Water and in Deuterium Oxide, Journal of the American Chemical Society 87(22), 5001 (1965).

Rogers et al., Paper-Like Electronic Displays: Large-Area Rubber-Stamped Plastic Sheets of Electronics and Microencapsulated Electrophoretic Inks, PNAS 98(9), p. 4835 (2001).

Smith et al., Phase Separation Within a Binary Self-Assembled Monolayer on Au{111} Driven by an Amide-Containing Alkanethiol, J. Phys. Chem. 105, 1119 (2001).

Solvents and Solvent Effects in Organic Chemistry, Second Edition, C. Reichardt, VCH Verlagsgesellschaft mbH, Germany (1988).

Srinivas et al., Bioanalytical Considerations for Compounds Containing Free Sulfhydryl Groups, Biomedical Chromotography vol. 17, pp. 285-291 (2003).

Svedhem et al., Synthesis of a Series of Oligo(Ethylene Glycol)-Terminated Alkanethiol Amides Designed to Address Structure and Stability of Biosensing Interfaces, J. Org. Chem. 66, 4494 (2001).

Takwa et al., One-Pot Difunctionalization of Poly(Omega-pentadecalactone) With Thiol-Thiol or Thiol-Acrylate Groups, Catalyzed by Candida Antarctica Lipase B, Macromol. Rapid Commun. 27, 1932 (2006).

Transene, Etchants, Feb. 5, 2014, Transene, p. 1-4.

(56) References Cited

OTHER PUBLICATIONS

Williams, Etch Rates for Micromachining Processing—Part II, J. Microelectromechanical Systems 12(6), p. 761 (2003).
Xia et al., A Selective Etching Solution for Use With Patterned Self-Assembled Monolayers of Alkanethiolates on Gold, Chem. Mater. 7, 2332 (1995).
Yazdi et al., Design of Highly CO2-Soluble Chelating Agents for Carbon Dioxide Extraction of Heavy Metals, J. Mater. Res., 1995, 10(3), pp. 530-537.
Research Disclosures, No. 40576, p. 81 (Jan. 1998).
International Search Report for PCT Application No. PCT/US2009/066337, mailed Mar. 5, 2010.

\* cited by examiner

US 9,688,649 B2

AMIDE-LINKED PERFLUOROPOLYETHER THIOL COMPOUNDS AND PROCESSES FOR THEIR PREPARATION AND USE

CROSS REFERENCE TO RELATED APPLICATIONS

This application is a divisional of U.S. patent application Ser. No. 13/132,673, filed Jun. 3, 2011, now allowed, which is a national stage filing under 35 U.S.C. 371 of PCT/US2009/066337, filed Dec. 2, 2009, which claims the priority of U.S. Provisional Application No. 61/121,598, filed Dec. 11, 2008, and U.S. Provisional Application No. 61/121,605, filed Dec. 11, 2008, the disclosures of which are incorporated by reference herein in their entirety.

FIELD

This invention relates to fluorinated thiol compounds and, in another aspect, to processes for their preparation.

BACKGROUND

Fluorinated polyethers (for example, perfluoropolyethers) have been used to prepare coating compositions for application to substrates (for example, hard surface substrates and fibrous substrates) to impart low surface energy characteristics such as oil and/or water repellency (oleophobicity and/or hydrophobicity). Thin films of perfluoropolyethers have also been used in various applications including use on magnetic recording media and/or electrical contacts (for example, as lubricants to reduce friction and wear, to protect surfaces from corrosion, and/or to allow conduction).

When used in coatings or films, however, many fluorinated polyethers have tended to diffuse to the surface of the coating or film and to become depleted over time (for example, due to repeated cleanings of the surface). This has led to the use of fluorinated polyether derivatives having reactive or functional groups (for example, fluorinated polyether thiols). The preparation of such functional derivatives has often required the use of complex, multi-step processes, the use of difficult-to-prepare intermediates, and/or has resulted in a product mixture rather than substantially purely the desired derivative compound.

SUMMARY

Thus, we recognize that there exists an ongoing need for fluorinated polyether derivatives that can meet the performance requirements of a variety of different applications, as well as for efficient and cost-effective processes for their preparation. Such processes will preferably be capable of flexibly and controllably producing compounds having tailored structures and physical properties, without producing a broad product mixture.

Briefly, in one aspect, this invention provides perfluoropolyether thiol compounds comprising a perfluoropolyether segment, at least one mercapto group (—SH), and at least one intervening divalent carbonylimino moiety (—C(=O)—N(R)—, wherein R is hydrogen or alkyl). Preferably, the perfluoropolyether segment is monovalent or divalent, the carbonylimino moiety is —C(=O)—NH— (that is, R is hydrogen), and/or the perfluoropolyether segment comprises at least one divalent hexafluoropropyleneoxy group (—CF(CF$_3$)—CF$_2$O—).

It has been discovered that a versatile new class of perfluoropolyether thiol compounds can be produced, for example, by a relatively simple one-step, ring-opening reaction of thiolactones (such as γ-thiobutyrolactone) with perfluoropolyether-substituted, primary or secondary amines. The resulting thiol compounds can be obtained in relatively pure form (with the major product being the desired thiol derivative from the ring opening), rather than in the form of a more complex product mixture.

In spite of their relatively flexible chain structure (which manifests itself in relatively wide liquid ranges), when applied to metal (for example, gold) surfaces in the form of a thin film (for example, a self-assembled monolayer), perfluoropolyether thiol compounds of the invention can exhibit high contact angles relative to those of fluoroalkyl thiols and perfluoroalkanesulfonyl-containing thiols (with or without an amide linkage). For example, the compounds can exhibit advancing contact angles as high as about 124 degrees with water and as high as about 75 degrees with hexadecane. The compounds can therefore be useful as fluorinated surface treatments to impart a relatively high degree of hydrophobicity and/or oleophobicity to a variety of metal substrates (for example, for surface protection, for mold release, to enhance ease of cleaning, or for use in microfluidic and microelectromechanical systems (MEMS) devices).

In addition, the compounds of the invention can be used in a number of other applications including, for example, use as polymerization chain transfer agents and as intermediates for the preparation of functional group-containing fluorochemical derivatives such as disulfides. Thus, at least some embodiments of the compounds of the invention meet the above-described, ongoing need for fluorinated polyether derivatives that can meet the performance requirements of a variety of different applications and can be efficiently and cost-effectively prepared.

In another aspect, this invention also provides the above-referenced process for preparing the compounds of the invention. The process comprises (a) providing at least one thiolactone compound; (b) providing at least one perfluoropolyether-substituted, primary or secondary amine compound (preferably, a compound that is amide-linked); and (c) combining the thiolactone compound and the perfluoropolyether-substituted, primary or secondary amine compound (preferably, in the presence of at least one tertiary amine).

In yet another aspect, this invention provides a process for using the compounds of the invention as polymerization chain transfer agents. The process comprises polymerizing at least one vinyl monomer (preferably, at least one fluorine-containing, vinyl monomer) in the presence of at least one polymerization initiator and at least one perfluoropolyether thiol compound of the invention.

In further aspects, this invention provides perfluoropolyether disulfide compounds (in the form of disulfide-linked dimers of the perfluoropolyether thiol compounds of the invention) and a process for their preparation. The process comprises oxidizing at least one perfluoropolyether thiol compound of the invention. The perfluoropolyether disulfide compounds comprise two perfluoropolyether segments (preferably, monovalent and thereby terminal) and at least one pair (preferably, only one pair) of intervening divalent carbonylimino moieties that are linked by, and bonded to, a central divalent dithio moiety. The perfluoropolyether disulfide compounds can be symmetrical or asymmetrical (or mixed), depending upon whether two identical or two different perfluoropolyether thiol compounds are used in forming the disulfide-linked dimer.

In other aspects, this invention further provides a surface treatment process and a surface-treated article. The process comprises (a) providing at least one substrate having at least one surface; (b) providing at least one treatment composition comprising at least one perfluoropolyether thiol or disulfide compound of the invention or a combination thereof; and (c) applying the treatment composition to at least a portion of at least one surface of the substrate. The article comprises at least one substrate having at least one surface bearing on at least a portion thereof at least one treatment composition comprising at least one perfluoropolyether thiol or disulfide compound of the invention, at least one product of reaction of the compound with the substrate, or a combination thereof

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range.

DEFINITIONS

As used in this patent application:

"amide-linked" means comprising at least one carbonylimino moiety (as defined below);

"catenated heteroatom" means an atom other than carbon (for example, oxygen, nitrogen, or sulfur) that is bonded to carbon atoms in a carbon chain so as to form a carbon-heteroatom-carbon chain;

"carbonylimino" means a divalent group or moiety of formula —C(=O)—N(R)—, wherein R is hydrogen or alkyl (for example, selected from alkyl groups having from one to about four carbon atoms);

"carbonyloxy" means a divalent group or moiety of formula —C(=O)O—;

"carbonylthio" means a divalent group or moiety of formula —C(=O)S—;

"dithio" means a divalent group or moiety of formula —S—S—;

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated;

"heteroalkylene" means an alkylene group or moiety containing at least one catenated heteroatom;

"mercapto" means a monovalent group or moiety of formula —SH;

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine;

"perfluoroether" means a group or moiety having two saturated or unsaturated perfluorocarbon groups (linear, branched, cyclic (preferably, alicyclic), or a combination thereof) linked with an oxygen atom (that is, there is one catenated oxygen atom);

"perfluoropolyether segment" means a group or moiety having three or more saturated or unsaturated perfluorocarbon groups (linear, branched, cyclic (preferably, alicyclic), or a combination thereof) linked with oxygen atoms (that is, there are at least two catenated oxygen atoms);

"sulfonamido" means a divalent group or moiety of formula —SO$_2$N(R')—, wherein R' is hydrogen or alkyl (for example, selected from alkyl groups having from one to about four carbon atoms); and "thio" means a divalent group or moiety of formula —S—.

Perfluoropolyether Thiol Compounds

The perfluoropolyether thiol compounds of the invention comprise a perfluoropolyether segment, at least one mercapto group (—SH), and at least one intervening or interposed divalent carbonylimino moiety (—C(=O)—N(R)—, wherein R is hydrogen or alkyl; preferably, the alkyl group has from one to about four carbon atoms). The divalent carbonylimino moiety can be directly or indirectly (preferably, directly) bonded through its carbon atom to the perfluoropolyether segment and indirectly bonded through its nitrogen atom to the mercapto group. Alternatively, the divalent carbonylimino moiety can be indirectly bonded through its carbon atom to the mercapto group and indirectly bonded through its nitrogen atom to the perfluoropolyether segment. The perfluoropolyether segment can be linear, branched, cyclic (preferably, alicyclic), or a combination thereof.

Preferably, the perfluoropolyether segment is monovalent or divalent, the carbonylimino moiety is —C(=O)—NH— (that is, R is hydrogen), and/or the perfluoropolyether segment comprises at least one divalent hexafluoropropyleneoxy group (—CF(CF$_3$)—CF$_2$O—). Preferred perfluoropolyether segments include F[CF(CF$_3$)CF$_2$O]$_a$CF(CF$_3$)—, wherein a has an average value of about 4 to about 20, and —CF(CF$_3$)(OCF$_2$CF(CF$_3$))$_b$OCF$_2$CF$_2$CF$_2$CF$_2$O(CF(CF$_3$)CF$_2$O)$_c$CF(CF$_3$)—, wherein b+c has an average value of about 4 to about 15. Such perfluoropolyether segments can be obtained through the oligomerization of hexafluoropropylene oxide and can be preferred because of their relatively benign environmental properties.

A class of the compounds of the invention is that which can be represented by the following general formula (I):

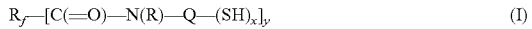

$$R_f\text{—[C(=O)—N(R)—Q—(SH)}_x]_y \qquad (I)$$

wherein $R_f$ is a monovalent or divalent perfluoropolyether group; R is hydrogen or alkyl; Q is a divalent, trivalent, or tetravalent organic linking group; x is an integer of 1 to 3 (preferably, 1); and y is an integer of 1 or 2 (preferably, 1). Preferably, R is hydrogen or an alkyl group having from one to about four carbon atoms (more preferably, hydrogen); and/or Q is a divalent group selected from alkylene, cycloalkylene, arylene, heteroalkylene, and combinations thereof (preferably, alkylene, heteroalkylene, and combinations thereof; more preferably, alkylene), optionally further comprising at least one divalent group selected from carbonyl, carbonyloxy, carbonylthio, carbonylimino, sulfonamido, and combinations thereof (preferably, carbonyl, carbonyloxy, carbonylimino, carbonylthio, and combinations thereof; more preferably, carbonyloxy, carbonylimino, and combinations thereof), and optionally being substituted with at least one moiety selected from alkyl, cycloalkyl, aryl, halo, and combinations thereof.

Preferably, Q has at least about 2 carbon atoms and/or less than or equal to about 30 carbon atoms (more preferably, less than or equal to about 20 carbon atoms; even more preferably, less than or equal to about 10 carbon atoms; most preferably, less than or equal to about 6 carbon atoms). Particularly preferred linking groups, Q, include —CH$_2$CH$_2$—, —CH$_2$CH$_2$CH$_2$—[NH—C(=O)]—CH$_2$CH$_2$CH$_2$—. —CH$_2$CH$_2$—[N(CH$_3$)—C(=O)]—CH$_2$CH$_2$CH$_2$—, —CH$_2$CH$_2$CH$_2$—[N(CH$_3$)—C(=O)]—

CH₂CH₂CH₂—S—C(=O)—CH₂CH₂CH₂—,
—CH₂CH₂—[NH—C(=O)]—CH₂CH₂CH₂—,
—CH₂CH₂—[O—C(=O)]—CH₂CH₂—, —(CH₂CH₂O)₂—[C(=O)]—CH₂CH₂—, and combinations thereof.

$R_f$ can be linear, branched, cyclic, or a combination thereof and can be saturated or unsaturated. Representative examples of useful $R_f$ groups include, but are not limited to, those that have perfluorinated repeating units selected from —$(C_pF_{2p})$—, —$(C_pF_{2p}O)$—, —$(CF(Z))$—, —$(CF(Z)O)$—, —$(CF(Z)C_pF_{2p}O)$—, —$(C_pF_{2p}CF(Z)O)$—, —$(CF_2CF(Z)O)$—, and combinations thereof, wherein p is an integer of 1 to about 10 (preferably, 1 to about 8; more preferably, 1 to about 6; even more preferably, 1 to about 4; most preferably, 1 to about 3); Z is selected from perfluoroalkyl, perfluoroether, perfluoropolyether, and perfluoroalkoxy groups that are linear, branched, cyclic, or a combination thereof and that have less than or equal to about 12 carbon atoms (preferably, less than or equal to about 10 carbon atoms; more preferably, less than or equal to about 8 carbon atoms; even more preferably, less than or equal to about 6 carbon atoms; still more preferably, less than or equal to about 4 carbon atoms; most preferably, less than or equal to about 3 carbon atoms) and/or less than or equal to about 4 oxygen atoms (preferably, less than or equal to about 3 oxygen atoms; more preferably, less than or equal to about 2 oxygen atoms; most preferably, zero or one oxygen atom). In these perfluoropolyether structures, different repeating units can be combined in a block, alternating, or random arrangement to form the $R_f$ group.

When $R_f$ is monovalent, its terminal group can be $(C_pF_{2p+1})$— or $(C_pF_{2p+1}O)$—, for example, wherein p is as defined above. Representative examples of useful monovalent $R_f$ groups include, but are not limited to, $C_3F_7O(CF(CF_3)CF_2O)_nCF(CF_3)$—, $C_3F_7O(CF_2CF_2CF_2O)_nCF_2CF_2$—, $CF_3O(C_2F_4O)_nCF_2$—, $CF_3O(CF_2O)_n(C_2F_4O)_qCF_2$— and $F(CF_2)_3O(C_4F_8O)_q(CF_2)_3$— (wherein n has an average value of 0 to about 50, about 1 to about 50, about 3 to about 30, about 3 to about 15, or about 3 to about 10; and q has an average value of 0 to about 50, about 3 to about 30, about 3 to about 15, or about 3 to about 10).

Representative examples of useful divalent $R_f$ groups include, but are not limited to, —$CF_2O(CF_2O)_n(C_2F_4O)_qCF_2$—, —$CF_2O(C_2F_4O)_qCF_2$—, —$(CF_2)_3O(C_4F_8O)_q(CF_2)_3$—, and —$CF(CF_3)(OCF_2CF(CF_3))_sOC_1F_2O(CF(CF_3)CF_2O)_qCF(CF_3)$— (wherein n and q are as defined above; s has an average value of 0 to about 50, about 1 to about 50, about 3 to about 30, about 3 to about 15, or about 3 to about 10; the sum of q and s (that is, q+s) has an average value of 0 to about 50 or about 4 to about 40; the sum of q and n (that is, q+n) is greater than 0; and t is an integer of about 2 to about 6).

A preferred class of the compounds of the invention is that which can be represented by the following general formula (II):

$R_f'$—$(O[CF(CF_3)CF_2O]_aCF(CF_3)$—$[C(=O)$—N(R)—Q—$(SH)_x])_y$ (II)

wherein $R_f'$ is a linear or branched perfluoroalkyl or perfluoroalkylene group (preferably, having from 1 to about 6 carbon atoms); a has an average value of about 4 to about 20; and R, Q, x, and y are as defined above in reference to general formula I.

Representative examples of the perfluoropolyether thiol compounds of the invention include the following, wherein a has an average value of about 4 to about 20 and b+c has an average value of about 4 to about 15:

F[CF(CF₃)CF₂O]ₐCF(CF₃)—C(=O)—NH—(CH₂)₃—N(CH₃)C(=O)—(CH₂)₃—SH,
F[CF(CF₃)CF₂O]ₐCF(CF₃)—C(=O)—NH—(CH₂)₂SH,
HS—(CH₂)₂—NH—C(=O)—CF(CF₃)(OCF₂CF(CF₃))ᵦ—OCF₂CF₂CF₂O(CF(CF₃)CF₂O)ᶜ—CF(CF₃)—C(=O)—NH—(CH₂)₂SH,
HS—(CH₂)₃—C(=O)—NH—(CH₂)₂—NH—C(=O)—CF(CF₃)(OCF₂CF(CF₃))ᵦ—OCF₂CF₂CF₂O(CF(CF₃)CF₂O)ᶜ—CF(CF₃)—C(=O)—NH—(CH₂)₂—NHC(=O)—(CH₂)₃—SH,
F[CF(CF₃)CF₂O]ₐCF(CF₃)—C(=O)NH—CH₂CH₂—O—C(=O)—CH₂CH₂SH,
F[CF(CF₃)CF₂O]ₐCF(CF₃)—C(=O)NH—(CH₂CH₂—O)₂—C(=O)—CH₂CH₂SH,
HS—(CH₂)₃—C(=O)—N(CH₃)—(CH₂)₃—NH—C(=O)—CF(CF₃)(OCF₂CF(CF₃))ᵦ—OCF₂CF₂CF₂O(CF(CF₃)CF₂O)ᶜ—CF(CF₃)—C(=O)—NH—(CH₂)₃—N(CH₃)C(=O)—(CH₂)₃—SH, and the like, and combinations thereof.

Preparation of Perfluoropolyether Thiol Compounds

The perfluoropolyether thiol compounds of the invention can be prepared by various different methods. For example, a perfluoropolyether derivative such as a methyl ester, an acid chloride, or an acid fluoride can be reacted with an amine-functional alkanethiol (for example, 2-aminoethanethiol) or a corresponding alkylammonium salt (for example, SH—CH₂CH₂—NH₃⁺Cl⁻) under basic conditions (for example, NaOH or KOH) in water. Such methods can provide, however, complex product mixtures comprising relatively low yields of the desired amide-linked perfluoropolyether thiol compound.

Thus, a preferred method of preparation is the process of the invention, which can provide the desired compound in relatively pure form as the major product of the ring opening of a thiolactone with an amine derivative of the corresponding perfluoropolyether. The process of the invention comprises (a) providing at least one thiolactone compound (preferably, a thiolactone compound having from about 5 to about 8 ring members; more preferably, from about 5 to about 6 ring members); (b) providing at least one perfluoropolyether-substituted, primary or secondary amine compound (preferably, one that is amide-linked); and (c) combining the thiolactone compound and the perfluoropolyether-substituted, primary or secondary amine compound (preferably, in the presence of at least one tertiary amine).

For example, at least one perfluoropolyether-substituted, primary or secondary amine, at least one thiolactone (generally at least a stoichiometric amount relative to the perfluoropolyether amine; preferably, a stoichiometric excess), and, optionally, at least one anhydrous, polar, aprotic solvent (for example, tetrahydrofuran (THF)) can be combined in essentially any order in any suitable reactor (for example, a round bottom flask equipped with a magnetic stir bar, a reflux condenser, and a nitrogen inlet), which can then be stirred and heated to a desired reaction temperature (for example, about 75° C.) under a nitrogen atmosphere. At least one tertiary amine (in at least a catalytic amount) can then be added to the reactor (or can be added continuously or in portions), generally with stirring or agitation of the reactor contents and, preferably, with temperature control.

After completion of tertiary amine addition, or after the reaction has run to completion, the reactor can be cooled and vented, and the reactor contents can be distilled to remove any excess thiolactone and any solvent. If desired, the resulting distilled product optionally can be further purified (for example, prior to spectroscopic analysis) by pouring the product into water and phase-separating the resulting mixture.

Perfluoropolyether-substituted, primary and secondary amine compounds suitable for use in carrying out the preparation process of the invention can be prepared by known methods. For example, a perfluoropolyether (as described above) derivative such as a methyl ester can be reacted with a diamine compound having at least one primary amino group (for example, a diaminoalkane having from about 2 to about 6 carbon atoms, such as 1,3-diaminopropane) under a nitrogen atmosphere.

Preferred perfluoropolyether derivatives for reaction with such diamines can be obtained by oligomerization of hexafluoropropylene oxide (HFPO). Such oligomerization provides a carbonyl fluoride derivative, which can be converted to a methyl ester or other derivative by known reactions (for example, those described in U.S. Pat. No. 3,250,808 (Moore et al.), the descriptions of which are incorporated herein by reference). The carbonyl fluoride derivative prepared by such oligomerization is in the form of a mixture of compounds of varying molecular weight having varying degrees of oligomerization (that is, the derivative is not synthesized as a single compound but as a mixture of compounds with different perfluoropolyether groups). Preferably, the mixture has a number average molecular weight of at least about 400 g/mole (more preferably, at least about 800 g/mole; most preferably, at least about 1000 g/mole). For example, the number average molecular weight of the mixture can be from 400 to 10000 g/mole, 800 to 4000 g/mole, or 1000 to 3000 g/mole.

Perfluoropolyether diacyl fluorides can be prepared by the photooxidative polymerization of tetrafluoroethylene (TFE), which results in the formation of perfluoropolyether polyperoxides. The perfluoropolyether polyperoxides can be reduced by physical techniques (for example, thermal or photochemical treatment) or by chemical techniques (for example, reduction with hydrogen in the presence of noble metal catalysts such as platinum or palladium). The reduction breaks the peroxidic perfluoropolyether bonds and can give perfluoropolyethers of lower molecular weight having —COF end groups and randomly-distributed difluoromethyleneoxy and tetrafluoroethyleneoxy moieties. This synthetic method is described in more detail, for example, in U.S. Patent Application Publication No. 2003/0013923 A1 (Marchionni et al.) and in U.S. Pat. No. 5,354,922 (Marchionni et al.), the descriptions of which are incorporated herein by reference.

Perfluoropolyether acyl fluorides can also be prepared by fluoride-catalyzed oligomerization of 1,1,2,2,-tetrafluorooxetane, followed by direct fluorination (as described, for example, in U.S. Pat. Nos. 4,904,417 and 4,845,268 (Ohsaka et al.), the description of which is incorporated herein by reference). These acyl fluorides can be converted to methyl esters by using the above-referenced procedures.

Thiolactone compounds suitable for use in carrying out the preparation process of the invention include those that are capable of undergoing a ring-opening reaction when combined with perfluoropolyether-substituted, primary or secondary amines. The thiolactones can be prepared by any of a variety of standard synthetic procedures that are well-known in the art. Some thiolactones (for example, gamma-butyrothiolactone) are also commercially available.

Representative examples of useful thiolactones include gamma-butyrothiolactone, delta-valerothiolactone, and the like, and mixtures thereof. (Mixtures can be used, if desired, but mixtures are generally less preferred due to the resulting production of product mixtures that can require purification.) Gamma-butyrothiolactone is a preferred thiolactone.

Tertiary amines suitable for use in carrying out the preparation process of the invention include those that are capable of catalyzing the reaction of thiolactones with perfluoropolyether-substituted, primary or secondary amines. Preferably, the tertiary amines have a relatively low boiling point. The tertiary amines can be prepared by any of a variety of methods that are well-known in the art, and many are commercially available.

Representative examples of useful tertiary amines include trialkylamines such as trimethylamine, triethylamine, and tripropylamine; pyridine; and the like; and combinations thereof. Preferred tertiary amines include trialkylamines (more preferably, trimethylamine, triethylamine, tripropylamine, and combinations thereof; most preferably, triethylamine).

Suitable solvents for use in carrying out the preparation process of the invention include anhydrous, polar, aprotic solvents such as glycol ether solvents (for example, glyme, diglyme, triglyme, tetraglyme, and the like, and mixtures thereof), tetrahydrofuran (THF), dimethylformamide, dimethyl sulfoxide, sulfolane, acetonitrile, and the like, and mixtures thereof. Preferred solvents include THF, glyme, diglyme, triglyme, tetraglyme, dimethylformamide, and mixtures thereof; with THF, glyme, diglyme, dimethylformamide, and mixtures thereof being more preferred and THF most preferred.

Use of Perfluoropolyether Thiol Compounds

The perfluoropolyether thiol compounds can be used alone or in admixture with each other or with commonly-used solvents (for example, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, hydrofluoroethers, and the like, and mixtures thereof). Such solvents are preferably at least partially fluorinated, can be chosen to modify or enhance the properties of a composition for a particular use, and can be utilized in ratios (of solvent(s) to perfluoropolyether thiol(s)) such that the resulting composition preferably has no flash point. If desired, the perfluoropolyether thiol compounds can be used in combination with other compounds that are very similar in properties relative to a particular use (for example, other fluorochemical thiol compounds) to form compositions that "consist essentially" of the perfluoropolyether thiol compounds of the invention.

Minor amounts of optional components can be added to the compounds to impart particular desired properties for particular uses. Useful compositions can comprise conventional additives such as, for example, surfactants, stabilizers, anti-oxidants, flame retardants, and the like, and mixtures thereof.

The perfluoropolyether thiol compounds of the invention (or a composition comprising, consisting, or consisting essentially thereof) can be used in various applications. For example, the compounds can be used as polymerization chain transfer agents, as intermediates for the preparation of functional group-containing fluorochemical derivatives such as disulfides, and as fluorinated surface treatments. In using the perfluoropolyether thiol compounds of the invention as chain transfer agents, the processes described in, for example, Research Disclosures, Number 40576, page 81 (January 1998) and in U.S. Pat. No. 5,182,342 (Feiring et al.) and U.S. Pat. No. 6,399,729 (Farnham et al.) can be used, the descriptions of which are incorporated herein. Such processes can comprise polymerizing at least one vinyl monomer (preferably, at least one fluorine-containing, vinyl monomer) in the presence of at least one polymerization initiator and at least one perfluoropolyether thiol compound of the invention.

The perfluoropolyether thiol compounds of the invention can also be used to prepare perfluoropolyether disulfides by carrying out the oxidation of the perfluoropolyether thiol compounds (for example, by bubbling air through the neat liquid or a solvent solution of the perfluoropolyether thiol at room temperature). Such oxidation can be useful to reduce the vapor pressure and/or control the odor of the perfluoropolyether thiol compounds.

In spite of their relatively flexible chain structure (which manifests itself in relatively wide liquid ranges), when applied to metal (for example, gold) surfaces in the form of a thin film (for example, a self-assembled monolayer), perfluoropolyether thiol compounds of the invention can exhibit high contact angles relative to those of fluoroalkyl thiols and perfluoroalkanesulfonyl-containing thiols (with or without an amide linkage). For example, the compounds can exhibit advancing contact angles as high as about 124 degrees with water and as high as about 75 degrees with hexadecane. The thiol compounds, as well as the above-described disulfide compounds, can therefore be useful as fluorinated surface treatments to impart a relatively high degree of hydrophobicity and/or oleophobicity to a variety of metal substrates (for example, for surface protection, for mold release, to enhance ease of cleaning, or for use in microfluidic and microelectromechanical systems (MEMS) devices).

In using the perfluoropolyether thiol and/or disulfide compounds of the invention (preferably, the thiols) as fluorinated surface treatments, useful methods generally include those that comprise exposure of the surface to be treated to a dilute solution of the perfluoropolyether thiol compound in an appropriate solvent for a period of time sufficient to allow formation of a fluorinated or functionalized region of the surface. Exposure times can vary widely (ranging, for example, from about a few seconds up to about 24 hours), depending upon the application.

Useful substrates for surface treatment include those that comprise at least one inorganic material (for example, a metallic or metal oxide material, including polycrystalline materials) alone or as a coating on a physical support such as, for example, a polymer film or a glass or silicon wafer. The inorganic material can include, for example, elemental metal, metal alloys, intermetallic compounds, metal oxides, metal sulfides, metal carbides, metal nitrides, and the like, and combinations thereof. Exemplary metals include gold, silver, palladium, platinum, rhodium, copper, nickel, iron, indium, tin, tantalum, and the like, as well as combinations thereof (for example, mixtures, alloys, and compounds of these elements). Preferred metals include silver, gold, copper, platinum, nickel, and combinations thereof (most preferably, gold).

The perfluoropolyether thiol and/or disulfide compounds of the invention (or compositions comprising the compounds, as described above) can be applied to at least a portion of at least one surface of the substrate by essentially any known or hereafter-developed surface treatment application method. For example, coating and printing methods such as dip coating, spin coating, spray coating, gravure printing, flexographic printing, inkjet printing, stamping, microcontact printing, and the like, and combinations thereof can be useful. Application methods that can provide self-assembled monolayer coatings can be preferred for at least some applications (for example, for use on nanostructured surfaces and in other applications where any potentially deleterious effects of the coating on optical, cosmetic, and/or electrical properties are desirably minimized).

As is known in the art, such application can include a displacement reaction that results in removal or modification of an atom or functional group in the compounds of the invention (for example, conversion of the thiol compound to a thiolate by removal of the hydrogen atom of the mercapto group of the thiol compound and formation of a bond between the sulfur atom of the mercapto group and a metal (for example, gold) substrate, as described, for example, by Love et al. in "Self-Assembled Monolayers of Thiolates on Metals as a Form of Nanotechnology," Chemical Reviews 105, 1103 (2005)). Thus, the resulting surface treatment can comprise molecules that are chemically different from the compounds in the surface treatment composition (such as products of reaction between the compounds and the substrate to which the composition is applied).

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials

Gamma-butyrothiolactone, mercaptoethanolammonium hydrochloride, triethylamine, N-methyl-1,3-diaminopropane, monoethanolamine, ethylenediamine, diisopropylethylamine, and methanesulfonyl chloride were obtained from Aldrich Chemical Company, Milwaukee, Wis. All solvents were standard reagent grade obtained from commercial sources and were used without further purification unless specified otherwise.

Unless otherwise noted, "HFPO—" refers to the monovalent end group $F(CF(CF_3)CF_2O)_aCF(CF_3)$— of the methyl ester $F(CF(CF_3)CF_2O)_aCF(CF_3)C(=O)OCH_3$, wherein "a" averaged about 6.7, and the methyl ester had an average molecular weight of about 1,211 g/mole. This methyl ester was prepared by essentially the method described in U.S. Pat. No. 3,250,808 (Moore et al.), the description of this method being incorporated herein by reference, with purification by fractional distillation. This methyl ester was converted to the amidol HFPO—$C(=O)NHCH_2CH_2OH$ by treatment with monoethanolamine, essentially as described in U.S. Patent Application Publication No. 2005/0250921 (Qiu et al) on pages 6 and 7 under the procedure for FC-4.

The dimethyl ester $CH_3O(O=)C—CF(CF_3)(OCF(CF_3)CF_2)_bOCF_2CF_2CF_2CF_2O—(CF_2CF(CF_3)O)_cCF(CF_3)—C(=O)OCH_3$, wherein b+c averaged about 8.4, was prepared using $FC(=O)CF_2CF_2C(=O)F$ as a starting material, essentially according to the method described in U.S. Pat. No. 3,250,807 (Fritz et al.), which provided the corresponding oligomeric bis-acid fluoride, followed by methanolysis and purification by removal of lower boiling materials by fractional distillation, essentially as described in U.S. Pat. No. 6,923,921 (Flynn et. al.), the descriptions of both methods being incorporated herein by reference. Unless otherwise noted, "—HFPO—" refers to the divalent oligomer —$CF(CF_3)(OCF(CF_3)CF_2)_bOCF_2CF_2CF_2CF_2O(CF_2CF(CF_3)O)_cCF(CF_3)$—, and thus the above-described dimethyl ester can be termed alpha, omega-HFPO—$[C(=O)OCH_3]_2$.

HFPO—C(=O)NH—CH$_2$CH$_2$CH$_2$—N(CH$_3$)H was prepared essentially as described in U.S. Pat. No. 7,335,786 (Iyer et al), Preparative Example 1.

HFPO[—C(=O)NH—CH$_2$CH$_2$—NH$_2$]$_2$ was prepared essentially as described in U.S. Pat. No. 7,335,786 (Iyer et al), Preparative Example 3.

HFPO—C(=O)NHCH$_2$CH$_2$OCH$_2$CH$_2$OH was prepared by the following procedure: A 500 mL round bottom flask equipped with magnetic stir bar, oil bath, reflux condenser, and nitrogen inlet was charged with HFPO—C(=O)OCH$_3$ (70 g, 0.0537 mole) and NH$_2$—CH$_2$CH$_2$—O—CH$_2$CH$_2$—OH (5.65 g, 1 molar equivalent) under a nitrogen atmosphere. The resulting mixture was allowed to stir at 75° C. for 16 hours. A sample of the mixture was then analyzed by infrared spectroscopy (IR) and proton ($^1$H) NMR, and the resulting spectral data confirmed formation of the desired product. The mixture was washed with brine (5×50 mL), and extracted with methyl t-butyl ether (MTBE). The resulting extract was dried over MgSO$_4$, filtered, stripped of solvent using rotary evaporation, and then kept under vacuum for 12 hours at room temperature.

C$_4$F$_9$SO$_2$N(CH$_3$)CH$_2$CH$_2$OH (MeFBSE) and HFE-7100 (methyl perfluorobutyl ether) were obtained from 3M Company, St. Paul, Minn.

C$_4$F$_9$SO$_2$—N(CH$_3$)CH$_2$CH$_2$—NH$_2$ was prepared by the following procedure: N-Methylnonafluorobutanesulfonamide (626 g, 2 moles, 3M Company, St. Paul, Minn.), 2-ethyl-2-oxazoline (198 g, 2 moles, Alfa Aesar, Ward Hill, Mass.), and sodium carbonate (17 g, 0.16 mole, EMD Chemicals, Gibbstown, N.J.) were combined and heated for 16 hours at 140° C. to form N-(2-(N-methylnonafluorobutanesulfonamido)ethyl)propionamide. This amide was twice extracted with 250 mL deionized water, heated for 18 hours at 100° C. with a mixture of 250 mL concentrated hydrochloric acid and 100 mL deionized water, extracted with 925 mL of 24 weight percent aqueous sodium hydroxide solution, extracted with 250 mL 10 weight percent aqueous sodium hydroxide solution, and distilled to provide N-(2-aminoethyl)-N-methylnonafluorobutanesulfonamide (538 g; 75 percent recovery; 94 percent pure by gas chromatography (GC); distilled at 104-109° C. under 2 mm Hg pressure).

Example 1

Synthesis of HFPO—C(=O)—NH—(CH$_2$)$_3$—N(CH$_3$)C(=O)—(CH$_2$)$_3$—SH (Perfluoropolyether Thiol Compound A)

A 50 mL round bottom flask equipped with magnetic stir bar, oil bath, reflux condenser, and nitrogen inlet was charged with HFPO—C(=O)NH—CH$_2$CH$_2$CH$_2$—N(CH$_3$)H (5 g, 0.0039 mole), gamma-butyrothiolactone (4.03 g, 10 molar equivalents) and tetrahydrofuran (THF) (25 g) under a nitrogen atmosphere. The resulting mixture was turbid and allowed to stir at room temperature for 5 minutes. Triethylamine (3.985 g, 10 molar equivalents) was added to the mixture dropwise by syringe at room temperature. The mixture became clear after the addition of triethylamine and was allowed to stir at 75° C. for 16 hours. Excess unreacted gamma-butyrothiolactone was distilled out under vacuum, and the resulting mixture was poured into ice water. The resulting organic phase was extracted with HFE-7100, dried over MgSO$_4$, and filtered. Removal of solvent under vacuum left a paste that was analyzed by nuclear magnetic resonance spectroscopy (NMR) and gas chromatography-mass spectrometry (GC-MS). The resulting spectral data were consistent with formation of the desired product.

Example 2

Synthesis of HFPO—C(=O)—NH—CH$_2$CH$_2$—SH (Perfluoropolyether Thiol Compound B)

A 500 mL round bottom flask equipped with magnetic stir bar, oil bath, reflux condenser, and nitrogen inlet was charged with HFPO—C(=O)OCH$_3$ (100 g, 0.0761035 mole) and NH$_2$—CH$_2$CH$_2$—SH (7.05 g, 1.2 molar equivalents) under a nitrogen atmosphere. The resulting mixture was allowed to stir at 75° C. for 16 hours. A sample of the mixture was then analyzed by infrared spectroscopy (IR) and proton ($^1$H) NMR, and the resulting spectral data confirmed formation of the desired product. The mixture was washed with CH$_2$Cl$_2$ (5×50 mL), and the CH$_2$Cl$_2$ washings were combined, dried over MgSO$_4$, filtered, and the resulting product was stripped of solvent under vacuum for 12 hours at room temperature.

Example 3

Synthesis of HFPO—C(=O)—NH—CH$_2$CH$_2$—O—C(=O)—CH$_2$CH$_2$—SH (Perfluoropolyether Thiol Compound C)

A 500 mL round bottom flask equipped with magnetic stir bar, oil bath, Dean-Stark apparatus, reflux condenser, and nitrogen inlet was charged with HFPO—C(=O)NHCH$_2$CH$_2$OH (100 g, 0.06463 mole), HO(O=)C—CH$_2$CH$_2$—SH (8.23 g, 0.077 mole), p-toluenesulfonic acid (13 g), and toluene (600 g) under a nitrogen atmosphere. The resulting mixture was allowed to reflux and stir for 16 hours. The mixture was cooled and filtered, and solvent was removed from the mixture by rotary evaporation. The resulting residue was washed with water (500 mL×6 times), and the resulting organic portion was dissolved in methyl t-butyl ether (MTBE) (500 mL), dried over MgSO$_4$, filtered, and stripped by rotary evaporation to provide the desired product in 73 percent yield.

Example 4

Synthesis of HFPO—C(=O)—NH—(CH$_2$CH$_2$—O)$_2$—C(=O)—CH$_2$CH$_2$—SH (Perfluoropolyether Thiol Compound D)

A 500 mL round bottom flask equipped with magnetic stir bar, oil bath, Dean-Stark apparatus, reflux condenser, and nitrogen inlet was charged with HFPO—C(=O)NHCH$_2$CH$_2$OCH$_2$CH$_2$OH (100 g, 0.0727 mole), HO(O=)C—CH$_2$CH$_2$—SH (9.65 g, 0.090 mole), p-toluenesulfonic acid (13 g), and toluene (600 g) under a nitrogen atmosphere. The resulting mixture was allowed to reflux and stir for 16 hours. The mixture was cooled and filtered, and solvent was removed from the mixture by rotary evaporation. The resulting residue was washed with water (500 mL×6 times), and the resulting organic portion was dissolved in MTBE (500 mL), dried over MgSO$_4$, filtered, and solvent stripped by rotary evaporation to provide the desired product in 82 percent yield.

Example 5

Synthesis of HFPO—[C(=O)—NH—(CH$_2$)$_2$SH]$_2$ (Perfluoropolyether Thiol Compound E)

A 500 mL round bottom flask equipped with magnetic stir bar, oil bath, reflux condenser, and nitrogen inlet was charged with alpha, omega-HFPO—[C(=O)OCH$_3$]$_2$ (50 g, 0.0325 mole) and NH$_2$—CH$_2$CH$_2$—SH (6.035 g, 2.4 molar equivalents) under a nitrogen atmosphere. The resulting mixture was allowed to stir at 75° C. for 16 hours. A sample of the mixture was analyzed by IR and $^1$H NMR, and the resulting spectral data confirmed formation of the desired product. The mixture was extracted with CH$_2$Cl$_2$ (5×50 mL), and the combined CH$_2$Cl$_2$ extracts were dried over MgSO$_4$, filtered, and stripped of solvent under vacuum for 12 hours.

Example 6

Synthesis of HFPO[—C(=O)—NH—(CH$_2$)$_2$—NHC(=O)—(CH$_2$)$_3$—SH]$_2$ (Perfluoropolyether Thiol Compound F)

A 250 mL round bottom flask equipped with magnetic stir bar, reflux condenser, and nitrogen inlet was charged with HFPO[—C(=O)NH—CH$_2$CH$_2$—NH$_2$]$_2$ (10 g, 0.00628 mole), gamma-butyrothiolactone (6.4 g, 20 molar equivalents), and THF (80 g) under a nitrogen atmosphere. The resulting mixture was turbid and allowed to stir at room temperature for 5 minutes. Triethylamine (6.3 g, 20 molar equivalents) was added to the mixture dropwise by syringe at room temperature. The mixture became clear after the addition of triethylamine and was allowed to stir at 75° C. for 16 hours. Excess unreacted gamma-butyrothiolactone was distilled out, and the resulting mixture was poured into ice water. The resulting organic phase was extracted into HFE-7100, dried over MgSO$_4$, filtered, and solvent stripped under vacuum at room temperature. The resulting paste was analyzed by NMR and GC-MS, and the resulting spectral data confirmed formation of the desired product.

Example 7

Synthesis of HFPO[—C(=O)—NH—(CH$_2$)$_3$—N(CH$_3$)C(=O)—(CH$_2$)$_3$—SH]$_2$ (Perfluoropolyether Thiol Compound G)

A 250 mL round bottom flask equipped with magnetic stir bar, reflux condenser, and nitrogen inlet was charged with HFPO[—C(=O)NH—CH$_2$CH$_2$—NH(CH$_3$)]$_2$ (10 g, 0.00617 mole), gamma-butyrothiolactone (6.4 g, 20 molar equivalents), and THF (80 g) under a nitrogen atmosphere. The resulting mixture was turbid and was allowed to stir at room temperature for 5 minutes. Triethylamine (6.3 g, 20 molar equivalents) was added to the mixture dropwise by syringe at room temperature. The mixture became clear after the addition of triethylamine and was allowed to stir at 75° C. for 16 hours. Excess unreacted gamma-butyrothiolactone was distilled out, and the resulting mixture was poured into ice water. The resulting organic phase was extracted into HFE-7100, dried over MgSO$_4$, filtered, and solvent stripped under vacuum at room temperature. The resulting paste was analyzed by NMR and GC-MS, and the resulting spectral data confirmed formation of the desired product.

Comparative Example 1

Synthesis of C$_4$F$_9$SO$_2$N(CH$_3$)CH$_2$CH$_2$—SH (Comparative Compound C-1)

A mixture of 35.7 g (0.1 mole) MeFBSE, 14.0 g diisopropylethylamine, and 200 mL dichloromethane was treated dropwise with 11.5 g methanesulfonyl chloride in 20 mL dichloromethane. After washing the treated mixture with water and drying over MgSO$_4$, solvent was removed from the mixture to leave 50.4 g white solid. The solid (8.7 g) was heated with 2.2 g thiourea in 10 mL glyme overnight at about 60° C., causing a precipitate to form. Ethyl ether was added to the precipitate-containing glyme, and the resulting mixture was filtered to provide 5.0 g isothiouronium salt. The salt was heated in dilute NaOH, and the resulting solution was acidified, preciptating the thiol as a white solid. GC/MS data on the solid confirmed formation of the desired product.

Comparative Example 2

Synthesis of C$_4$F$_9$SO$_2$N(CH$_3$)CH$_2$CH$_2$NH—C(=O)—CH$_2$CH$_2$CH$_2$SH (Comparative Compound C-2)

A 250 mL round bottom flask equipped with magnetic stir bar, oil bath, reflux condenser, and nitrogen inlet was charged with C$_4$F$_9$SO$_2$N(CH$_3$)CH$_2$CH$_2$NH$_2$ (10 g, 0.028 mole), gamma-butyrothiolactone (28.083 g, 10 molar equivalents), and THF (75 g) under a nitrogen atmosphere. The resulting mixture was turbid and was allowed to stir at room temperature for 5 minutes. Triethylamine (28.3 g, 10 molar equivalents) was added to the mixture dropwise by syringe at room temperature. The mixture became clear after the addition of triethylamine and was allowed to stir at 75° C. for 16 hours. Excess gamma-butyrothiolactone was distilled out, and the resulting mixture was poured into ice water. The resulting organic phase was extracted in CH$_2$Cl$_2$, the washings were combined and dried over MgSO$_4$, and solvent was stripped under vacuum. The resulting product was analyzed by NMR and GC-MS, and the resulting spectral data confirmed formation of the desired product.

Comparative Example 3

Synthesis of C$_4$F$_9$SO$_2$N(CH$_3$)CH$_2$CH$_2$OC(=O)CH$_2$CH$_2$SH (Comparative Compound C-3)

A mixture of MeFBSEA (10 g, 0.028 mole), SH—CH$_2$CH$_2$—COOH (3.56 g, 0.0336 mole), and p-toluenesulfonic acid (PTSA) (1 g, 10 weight percent based on starting alcohol) was refluxed in toluene. Reaction of the mixture was monitored by IR, and, after the disappearance of an alcohol peak, the toluene was distilled out and the resulting product was added into brine. The resulting organic portion was extracted with dichloromethane, washed with water, and dried over MgSO$_4$.

Examples 8-15 and Comparative Examples 4 and 5

Surface Treatment

Substrates (gold-coated silicon wafers or gold-coated glass slides) were exposed to air plasma in a Harrick PDC-3×G plasma cleaner/sterilizer (available from Harrick Scientific Corporation, Ossining, N.Y.) for 3 minutes, then immersed in solutions of 0.1 weight percent surface treatment compound (a perfluoropolyether thiol compound of the invention or a comparative compound) in denatured ethanol at room temperature for the periods of time specified in Tables 1-3 below. The substrates were then rinsed in fresh denatured ethanol, dried under nitrogen, and subjected to dynamic contact angle measurements using water and hexadecane as wetting liquids. Contact angles were measured using a VCA-2500XE video contact angle apparatus (available from AST Products, Billerica, Mass.). Reported contact angle values are averages of measurements on the left and right sides of at least three drops. Drop volumes were 5 microliters for static measurements, and 1-3 microliters for advancing and receding measurements. Static contact angles were not reported for hexadecane, as they were generally found to be very close to the advancing contact angles.

TABLE 1

| | | SUBSTRATE: Gold-Coated Glass Slide (Immersion Time of 22 Hours) | | |
|---|---|---|---|---|
| Example No. | Surface Treatment Compound | Water Static Contact Angle (degrees) ± 1 Standard Deviation | Water Advancing Contact Angle (degrees) ± 1 Standard Deviation | Water Receding Contact Angle (degrees) ± 1 Standard Deviation |
| 8 | A | 112.2(+/−)0.2 | 114.2(+/−)0.4 | 96.2(+/−)1.1 |
| 9 | B | 110.9(+/−)0.7 | 114.5(+/−)0.1 | 90.5(+/−)2.2 |
| 10 | C-2 | 106.6(+/−)0.2 | 116.6(+/−)0.4 | 91.5(+/−)1.3 |
| 11 | E | 102.4(+/−)0.2 | 102.2(+/−)1.0 | 58.3(+/−)0.2 |
| 12 | C-1 | 104.4(+/−)0.2 | 111.9(+/−)0.4 | 91.8(+/−)1.6 |
| 13 | F | 106.7(+/−)0.2 | 111.0(+/−)2.6 | 81.7(+/−)0.9 |

TABLE 2

| | | SUBSTRATE: Gold-Coated Silicon Wafer (Immersion Time of 22 Hours) | | |
|---|---|---|---|---|
| Example No. | Surface Treatment Compound | Water Static Contact Angle (degrees) ± 1 Standard Deviation | Water Advancing Contact Angle (degrees) ± 1 Standard Deviation | Water Receding Contact Angle (degrees) ± 1 Standard Deviation |
| 8 | A | 112.6(+/−)0.2 | 124.8(+/−)0.6 | 97.5(+/−)1.0 |
| 9 | B | 110.1(+/−)0.2 | 114.5(+/−)0.2 | 75(+/−)1.0 |
| 10 | C-2 | 106.5(+/−)0.3 | 120.5(+/−)0.4 | 92.3(+/−)1.4 |
| 11 | E | 103.7(+/−)0.3 | 101.4(+/−)0.3 | 51.7(+/−)0.8 |
| 12 | C-1 | 101.3(+/−)0.2 | 112.8(+/−)1.1 | 81.7(+/−)0.9 |
| 13 | F | 107.8(+/−)0.5 | 110.1(+/−)0.3 | 52.5 (+/−)0.4 |

TABLE 3

| | | SUBSTRATE: Gold-Coated Glass Slide (Immersion Time of 4 Hours) | | | SUBSTRATE: Gold-Coated Glass Slide (Immersion Time of 4 Hours) | |
|---|---|---|---|---|---|---|
| Example No. | Surface Treatment Compound | Water Static Contact Angle (degrees) ± 1 Standard Deviation | Water Advancing Contact Angle (degrees) ± 1 Standard Deviation | Water Receding Contact Angle (degrees) ± 1 Standard Deviation | Hexadecane Advancing Contact Angle (degrees) ± 1 Standard Deviation | Hexadecane Receding Contact Angle (degrees) ± 1 Standard Deviation |
| 14 | C | 112.8 ± 0.3 | 119.7 ± 0.1 | 105.5 ± 1.2 | 77.2 ± 2.0 | 70.4 ± 0.4 |
| 15 | G | 101.3 ± 0.3 | 107.7 ± 0.7 | 79.3 ± 2.2 | 67.5 ± 1.2 | 60.0 ± 2.3 |
| C-4 | C-3 | 104.7 ± 0.8 | 114.6 ± 0.3 | 89.5 ± 0.1 | 73.1 ± 2.5 | 63.7 ± 1.2 |
| C-5 | None | 71 (single drop) | Not Measured | Not Measured | Not Measured | Not Measured |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows.

We claim:

1. A perfluoropolyether thiol compound comprising (a) a monovalent or divalent perfluoropolyether segment that comprises one or two divalent polyhexafluoropropyleneoxy group, (b) at least one mercapto group, and (c) at least one intervening divalent carbonylimino moiety, —C(=O)—NH—, that is directly or indirectly bonded through its carbon atom to said perfluoropolyether segment and indirectly bonded through its nitrogen atom to said mercapto group; wherein said compound is one of a class that is represented by the following general formula (II):

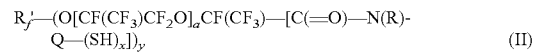

wherein $R_f'$ is a linear or branched perfluoroalkyl or perfluoroalkylene group; a has an average value of 4 to 20; R is hydrogen; Q is a divalent organic linking group selected from —CH$_2$CH$_2$CH$_2$—[NH—C(=O)]—CH$_2$CH$_2$CH$_2$—, —CH$_2$CH$_2$CH$_2$—[N(CH$_3$)—C(=O)]—CH$_2$CH$_2$CH$_2$—, —CH$_2$CH$_2$—[NH—C (=O)]—CH$_2$CH$_2$CH$_2$—, —CH$_2$CH$_2$—[O—C(=O)]—CH$_2$CH$_2$—, —(CH$_2$CH$_2$O)$_2$—[C(=O)]—CH$_2$CH$_2$—, and combinations thereof; x is an integer of 1; and y is an integer of 1 or 2.

2. The compound of claim 1, wherein said compound is selected from

F[CF(CF$_3$)CF$_2$O]$_a$CF(CF$_3$)—C(=O)—NH—(CH$_2$)$_3$—N(CH$_3$)C(=O)—(CH$_2$)$_3$—SH,

HS—(CH$_2$)$_3$—C(=O)—NH—(CH$_2$)$_2$—NH—C(=O)—CF(CF$_3$)(OCF$_2$CF(CF$_3$))$_b$—OCF$_2$CF$_2$CF$_2$O(CF(CF$_3$)CF$_2$O)$_c$—CF(CF$_3$)—C(=O)—NH—(CH$_2$)$_2$—NHC(=O)—(CH$_2$)$_3$—SH,

F[CF(CF$_3$)CF$_2$O]$_a$CF(CF$_3$)—C(=O)NH—CH$_2$CH$_2$—O—C(=O)—CH$_2$CH$_2$SH,

F[CF(CF$_3$)CF$_2$O]$_a$CF(CF$_3$)—C(=O)NH—(CH$_2$CH$_2$O)$_2$—C(=O)—CH$_2$CH$_2$SH, and mixtures thereof, wherein a has an average value of 4 to 20 and b+c has an average value of 4 to 15.

* * * * *

UNITED STATES PATENT AND TRADEMARK OFFICE
CERTIFICATE OF CORRECTION

PATENT NO.       : 9,688,649 B2
APPLICATION NO.  : 14/527877
DATED            : June 27, 2017
INVENTOR(S)      : Suresh Iyer Page 1 of 1

It is certified that error appears in the above-identified patent and that said Letters Patent is hereby corrected as shown below:

In the Specification

Column 3,
Line 11, after "thereof" insert -- . --.

Column 4,
Line 66, delete "$CH_2CH_2CH_2$-." and insert -- $CH_2CH_2CH_2$-, --, therefor.

Column 5,
Line 46, delete "$(CF_3))_8OC_1$" and insert -- $(CF_3))_8OC_t$ --, therefor.

Column 9,
Line 63, delete "inkjet" and insert -- ink-jet --, therefor.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*